US007826900B2

(12) United States Patent
Stellar et al.

(10) Patent No.: US 7,826,900 B2
(45) Date of Patent: Nov. 2, 2010

(54) APPARATUS FOR DIAGNOSING MUSCULAR PAIN AND METHOD OF USING SAME

(75) Inventors: Ryan M. Stellar, Center Valley, PA (US); Jeckin Shah, North Bergen, NJ (US); Daniel Silva, North Bergen, NJ (US); Norman J. Marcus, New York, NY (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 433 days.

(21) Appl. No.: 11/384,131

(22) Filed: Mar. 17, 2006

(65) Prior Publication Data
US 2006/0224210 A1    Oct. 5, 2006

Related U.S. Application Data

(60) Provisional application No. 60/663,125, filed on Mar. 18, 2005.

(51) Int. Cl.
*A61N 1/00*    (2006.01)
(52) U.S. Cl. .......................................... 607/46; 607/69
(58) Field of Classification Search ............. 607/46–47, 607/68–69, 115, 149–152
See application file for complete search history.

(56) References Cited

U.S. PATENT DOCUMENTS 4,177,819 A * 12/1979 Kofsky et al. ............... 607/63
4,431,002 A *  2/1984 Maurer et al. ............... 607/46
4,580,570 A *  4/1986 Sarrell et al. ............... 607/63
4,667,513 A    5/1987 Konno
4,697,599 A   10/1987 Woodley et al.

(Continued)

FOREIGN PATENT DOCUMENTS

DE           42 06 245 A1    9/1993

(Continued)

OTHER PUBLICATIONS

David G. Simons, "Myofascial Pain Syndromes Due to Trigger Points", Pain & Disability: Clinical, Behavioral & Public Policy Perspectives (1987), pp. 285-292.

(Continued)

*Primary Examiner*—Mark W Bockelman
(74) *Attorney, Agent, or Firm*—Greenberg Traurig, LLP

(57) ABSTRACT

Apparatus and method for diagnosing a source of muscular pain, wherein the apparatus includes a housing, an electrical signal generator mounted within the housing, and a pair of electrodes, one of which is mounted on one end of the housing and the other of which is mounted on an opposite end of the housing. The generator may include either an analog waveform generator or a digital signal processor. Each of the electrodes stimulates a muscle with an electrical signal generated by the generator. One of the electrodes has a relatively small contact area for targeting smaller muscles or muscle groups, while the other electrode has a relatively large contact area for targeting larger muscles or muscle groups. The apparatus is a self-contained, wireless unit and is highly maneuverable, which allows a user to quickly and easily diagnose a source of muscle pain.

2 Claims, 6 Drawing Sheets

U.S. PATENT DOCUMENTS

| | | | |
|---|---|---|---|
| 4,759,368 | A | 7/1988 | Spanton et al. |
| 5,425,751 | A | 6/1995 | Baeten et al. |
| 5,514,167 | A | 5/1996 | Smith et al. |
| 5,558,623 | A | 9/1996 | Cody |
| 5,653,739 | A | 8/1997 | Maurer et al. |
| 5,674,261 | A * | 10/1997 | Smith ............... 607/46 |
| 5,797,854 | A | 8/1998 | Hedgecock |
| D403,421 | S | 12/1998 | Cody et al. |
| 5,938,690 | A | 8/1999 | Law et al. |
| 6,044,303 | A | 3/2000 | Agarwala et al. |
| 6,146,334 | A | 11/2000 | Laserow |
| 6,292,701 | B1 | 9/2001 | Prass et al. |
| 6,393,328 | B1 * | 5/2002 | McGraw et al. ............ 607/72 |
| 6,432,063 | B1 | 8/2002 | Marcus |
| 6,584,358 | B2 * | 6/2003 | Carter et al. ............ 607/69 |
| 6,678,550 | B2 | 1/2004 | Hubbard, Jr. |
| 6,692,444 | B2 | 2/2004 | Gozani et al. |
| 6,757,558 | B2 | 6/2004 | Lange et al. |
| 6,871,100 | B2 | 3/2005 | Ciaff |
| 2002/0042590 | A1 | 4/2002 | Hubbard, Jr. |
| 2003/0045808 | A1 | 3/2003 | Kaula et al. |
| 2003/0171785 | A1 | 9/2003 | Duncan et al. |
| 2004/0126746 | A1 | 7/2004 | Toly |
| 2004/0236221 | A1 | 11/2004 | Wlicox et al. |
| 2004/0254610 | A1 | 12/2004 | Lin |
| 2005/0154329 | A1 | 7/2005 | Shimazu et al. |

FOREIGN PATENT DOCUMENTS

| | | | |
|---|---|---|---|
| EP | 0 158 336 | A2 | 10/1985 |
| EP | 1059064 | A2 | 12/2000 |
| WO | 01/13793 | A1 | 3/2001 |

OTHER PUBLICATIONS

R. D. Gerwin, "The Clinical Assessment of Myofascial Pain", in Handbook of Pain Assessment (1992), ed. by D. C. Turk, et al., The Guilford Press, New York, pp. 61-70.

Robert D. Gerwin, et al., "Interrater Reliability in Myofascial Trigger Point Examination", Pain (1997) 69:65-73.

Hans Kraus, et al., "The Reintroduction of an Exercise Program to Directly Treat Low Back Pain of Muscular Origin", Journal of Back and Musculoskeletal Rehabilitation (1997) 8:95-107.

Marek B. Wyszynski, "The New York Pain Treatment Program Protocol: A Structured Physical Therapy Approach for Treating the Muscular Components of Chronic Pain Syndromes", Journal of Back and Musculoskeletal Rehabilitation (1997) 8:109-123.

"Rich-Mar Theramini 2 Operation Handbook and Manual", Part # MN 2429, Rev. E, Batch 001.

"Theramini 3C Combination", http://www.richmarweb.com/theramini3c.htm.

"TENS 2000", http://www.ib3health.com/products/TensandEMS/ME/TENS2000.shtml.

Communication pursuant to Article 94(3) EPC in European Patent Application No. 06738844.7 dated May 26, 2009.

International Preliminary Report on Patentability, issued on Sep. 18, 2007 in International (PCT) Application No. PCT/US2006/009840.

National Institute of Standards and Technology (NIST), "Time and Frequency from A to Z: Am to B", NIST web page, printed on Oct. 27, 2009 from http://tf.nist.gov/general/enc-am.htm.

Extended European Search Report for EP 09176229.4 dated Jan. 21, 2010.

\* cited by examiner

APPARATUS FOR DIAGNOSING MUSCULAR PAIN AND METHOD OF USING SAME

CROSS-REFERENCE TO RELATED APPLICATION

This application claims the benefit of U.S. Provisional Patent Application No. 60/663,125 filed Mar. 18, 2005, entitled "Dynamic Mode Surface Electro-Neural Stimulator for Diagnosis of Muscle Pain," the disclosure of which is incorporated herein by reference in its entirety.

FIELD OF THE INVENTION

The present invention relates to apparatus for diagnosing muscle pain and, more particularly, to apparatus that employ electrical stimulation to accurately diagnose the source of muscle pain.

BACKGROUND OF THE INVENTION

A common type of musculoskeletal pain is myofascial pain syndrome, which is pain that emanates from muscles and corresponding connective tissue. Myofascial pain syndrome is often caused by myofascial pain generators called "trigger points." Trigger points are discrete, focal, irritable spots located in a taut band of skeletal muscle, i.e., a ropey thickening of the muscle tissue. A trigger point is often characterized by a "referred pain" pattern that is similar to the patient's pain complaint. Referred pain is felt not at the site of the trigger point origin, but remote from it. The pain is often described as spreading or radiating. A trigger point develops due to any number of causes, such as sudden trauma or injury to musculoskeletal tissue, fatigue, excessive exercising, lack of activity, tension or stress, and nutritional deficiencies.

A problem in treating myofascial pain syndrome is locating the trigger point, since pain is typically felt remote from the trigger point. A common technique for locating a trigger point is palpation. That is, a physician palpates a muscle region suspected of having a trigger point by applying manual pressure to the region with his finger tips and kneading the muscles. As the physician palpates the muscles, the patient verbally indicates the existence of any pain or sensitivity and whether it increases or decreases as the physician moves his fingers within the suspected region. A shortcoming of this manual technique is that it can only locate a trigger point with a slight degree of certainty, and cannot typically locate the specific muscle that contains the trigger point. In addition, there is no standard unit of pressure to exert when palpitating a muscle, which could lead to a misdiagnosis.

Other techniques to locate trigger points include the use of a palpation index, pressure threshold meters, thermographic measuring devices, and electromyographic identification. However, these techniques are difficult to learn and use and are not always reliable.

U.S. Pat. No. 6,432,063 to Marcus (hereinafter "the Marcus '063 Patent"), the entirety of which is incorporated herein by reference, discloses a method for locating myofascial trigger points (the "Marcus Method") by applying an electrical stimulus in a suspected muscle area containing a trigger point. As the electrical stimulus is moved about the muscle area, the patient indicates an increase or decrease in the level of pain and sensitivity. Once the maximum pain location has been located, the trigger point has been identified and, thus, it can be treated appropriately. However, the Marcus '063 Patent does not disclose in detail a particular electrical stimulator device that can be appropriately used in connection with the Marcus Method.

There are numerous trans-cutaneous electroneural stimulation (TENS) portable devices available in the marketplace. However, the leads (i.e., the electrodes) of these devices are designed for static and therapeutic purposes, rather than dynamic diagnosis purposes. As a result, TENS devices are not appropriate for locating myofascial trigger points.

U.S. Pat. No. 4,697,599 to Woodley et al. (the "Woodley '599 Patent") discloses a handheld meter for locating and detecting pain based on the measurement of conductance of skin in the area of perceived pain. The meter includes a housing, two concentric electrodes that extend from the housing, an electrical circuit connected to the electrodes, and a speaker. The electrodes are placed against a patient's skin at the location where a measurement is desired. The electrical circuit generates an electrical signal having a pulse frequency that varies according to the measured conductance of the skin. The conductance is measured aurally by a speaker, which translates the pulses into audible sounds, i.e., "clicks". The clicks increase in frequency as the conductance of the patient's skin increases, which indicates the location of pain. However, the Woodley '599 Patent does not disclose any correlation between increased conductance and the location of myofascial trigger points; and, therefore, the device is not effective at locating same.

U.S. Pat. No. 5,558,623 to Cody (the "Cody '623 Patent) discloses a therapeutic ultrasonic device, which includes a hammer-shaped applicator having a head with two diametrically-opposed diaphragms. A piezoelectric crystal is connected to each of the diaphragms, which convert electrical energy into ultrasonic energy. The handle is connected electrically (i.e., hard-wired) to a control console, which allows a user to control the operational functions of the applicator, such as frequency, intensity, mode of operation, etc. The Cody '623 Patent relates to the THERAMINI™ 3C brand clinical stimulator/ultrasound combination unit manufactured by Rich-Mar Corporation. However, the device disclosed in the Cody '623 Patent utilizes ultrasound signals for therapeutic purposes, and is not equipped for diagnostic purposes. In addition, the device is not portable; and, therefore, its ease of use in a clinical setting is limited.

Until now, there is no current device that effectively locates a myofascial trigger point. As a result, this has contributed to ignoring muscles as a major cause of most common pain problems and, unfortunately, has led to unnecessary testing, injections and medications, and surgeries. Accordingly, there is a need for a device that can accurately diagnose and locate trigger points, which is portable and ergonomically designed.

SUMMARY OF THE INVENTION

The problems and disadvantages associated with the prior art are overcome by the present invention, which includes an electro-neural stimulator for locating myofascial pain trigger points. The stimulator includes a housing, an electrical signal generator mounted within the housing, and a pair of electrodes, one of which is mounted to one end of the housing and the other of which is mounted to an opposite end of the housing. Each of the electrodes stimulates muscles with an electrical signal generated by the generator. A patient's response to such stimulus (i.e., whether such stimulus causes pain or sensitivity) is indicative of the existence or lack of a trigger point within the muscle. One of the electrodes has a relatively small surface area for diagnosing smaller muscles or muscle groups, while the other electrode has a relatively large surface area for diagnosing larger muscles or muscle groups. The stimulator is a self-contained, wireless unit and is highly maneuverable. These characteristics allow a user to quickly and easily diagnose a source of muscle pain.

In accordance with another aspect of the present invention, the housing is sized and shaped for mounting on a user's arm, while one of the electrodes is attached to a ring that is worn on the user's finger. This configuration allows the user to alternate quickly and easily between manual palpation of the subject muscle with his hand and fingertips and electrical stimulation of the muscle with the electrode.

In accordance with another aspect of the present invention, the generator may include an analog waveform generator or a digital signal processor. The properties of the electrical signal generated by the generator, such as waveform, amplitude, frequency and duty cycle, is selectable by the user.

Specifically, the present invention has been adapted for use in diagnosing the existence of myofascial trigger points. However, the present invention can be utilized to diagnose other sources of muscle pain, such as muscle tender points and tension.

Further features and advantages of the invention will appear more clearly on a reading of the following detailed description of the exemplary embodiments of the invention, which are given below by way of example only with reference to the accompanying drawings.

BRIEF DESCRIPTION OF THE DRAWINGS

For a more complete understanding of the present invention, reference is made to the following detailed description of the exemplary embodiments considered in conjunction with the accompanying drawings, in which.

DETAILED DESCRIPTION OF THE DRAWINGS

Figure 1:
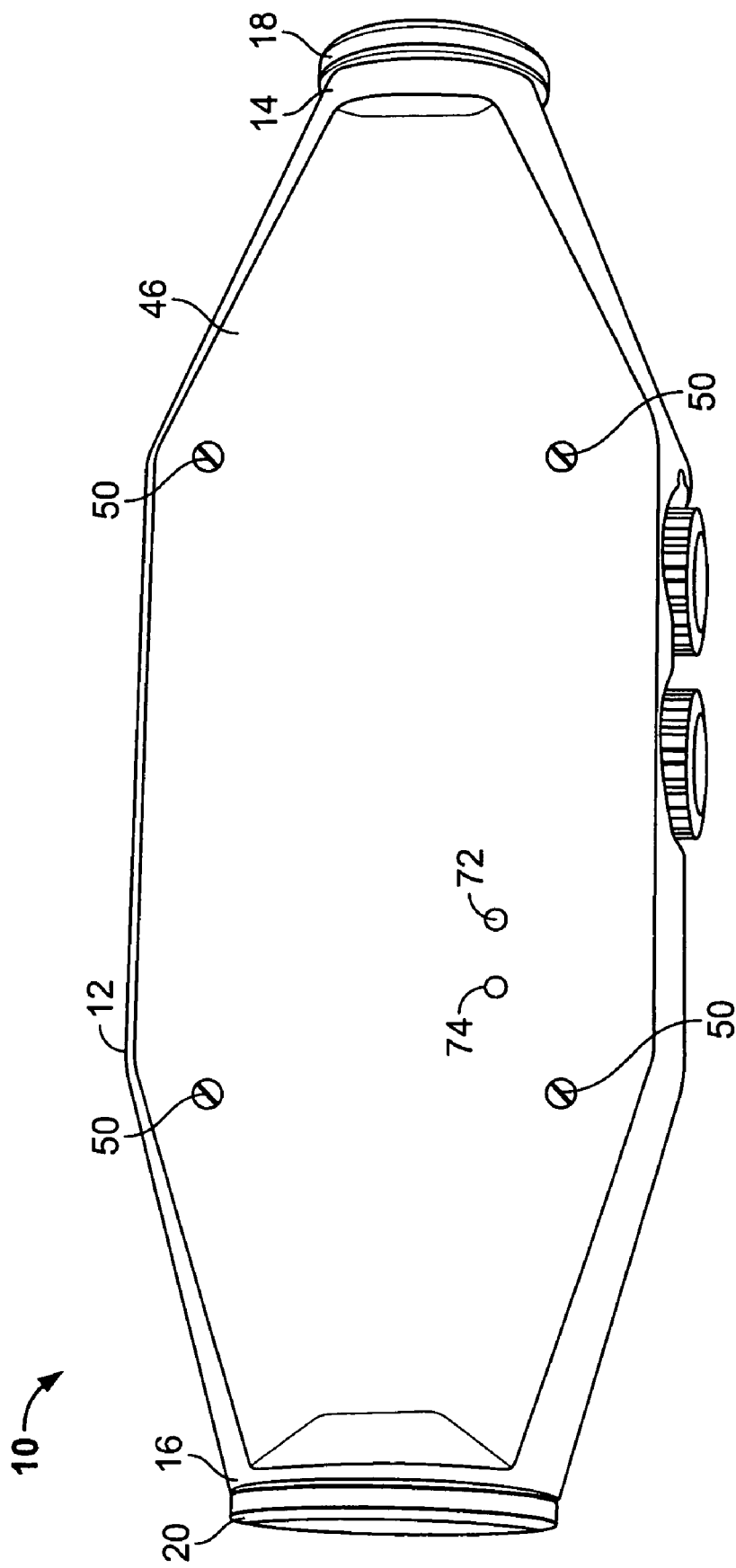
FIG. 1 is a top perspective view of an electro-neural stimulator constructed in accordance with one exemplary embodiment of the present invention.
Figure 2:
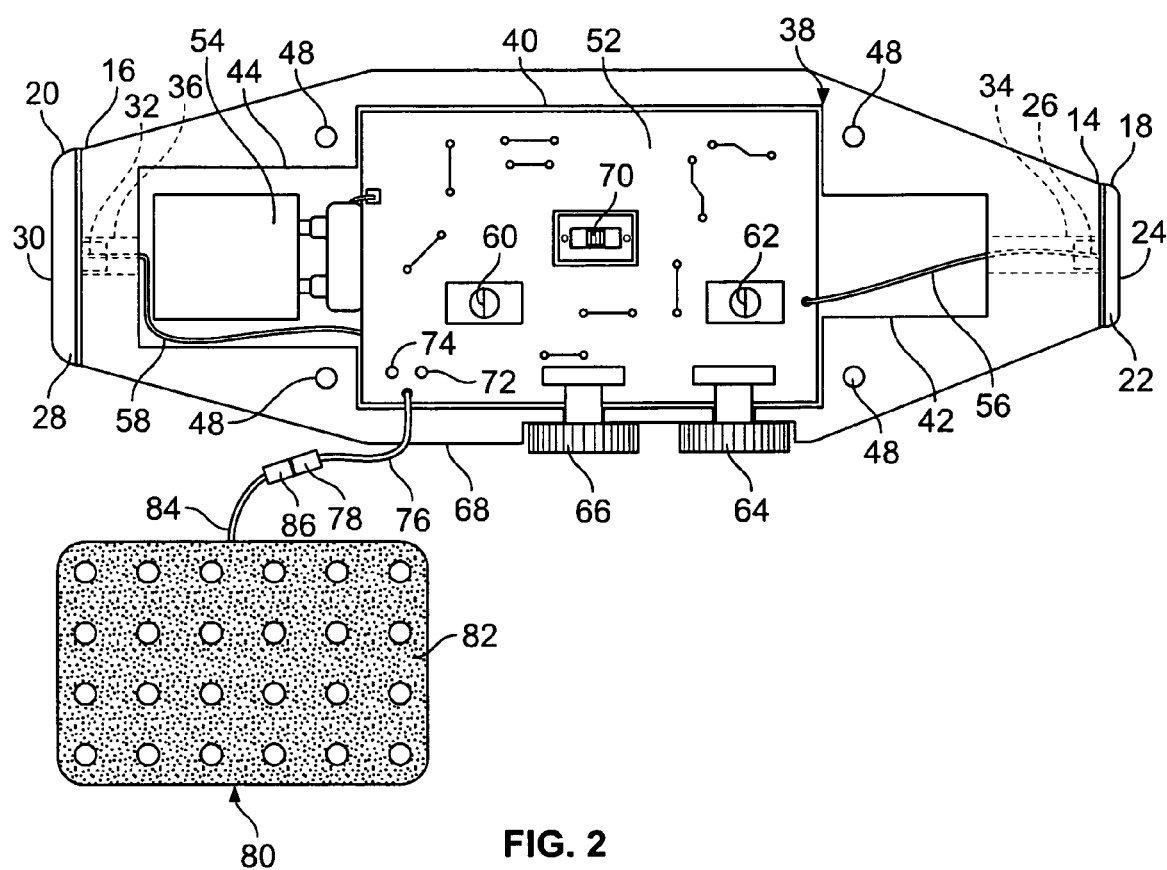
FIG. 2 is a top plan view of the stimulator shown in FIG. 1, with an access panel employed by the stimulator removed therefrom and a grounding electrode employed by the stimulator attached thereto.

Referring to FIGS. 1 and 2, an electro-neural stimulator 10 includes a hexagonal-shaped housing 12 having a first end 14 and a second end 16 opposite the first end 14. A first electrode 18 is mounted on the first end 14 of the housing 12, while a second electrode 20 is mounted on the second end 16 of the housing 12. With particular reference to FIG. 2, the first electrode 18 includes a circular-shaped head 22 having a contact surface 24 and a centrally located cylindrical-shaped pin 26 extending outwardly from the head 22. Similarly, the second electrode 20 includes a circular-shaped head 28 having a contact surface 30, and a centrally located cylindrical-shaped pin 32 extending outwardly from the head 28. The first end 14 of the housing 12 includes a cylindrical-shaped aperture 34 that extends axially therethrough 12. Similarly, the second end 16 of the housing 12 includes a circular-shaped aperture 36 that extends axially therethrough. The aperture 34 is sized and shaped to receive the pin 26 of the first electrode 18, while the aperture 36 is sized and shaped to receive the pin 32 of the second electrode 20. The first and second electrodes 18, 20 are secured to the housing 12 by friction fit or an adhesive. Alternatively, each of the pins 26, 32 of the first and second electrodes 18, 20, respectively, may include external threads, and each the apertures 34, 36 of the housing 12 may include internal threads such that the pins 26, 32 threadedly engage the apertures 34, 36, respectively (not shown in the Figures).

Preferably, the diameter of the head 28 of the second electrode 20 is greater than the diameter of the head 22 of the first electrode 18. Alternatively, the diameter of the head 28 of the second electrode 20 can be smaller than the diameter of the head 22 of the first electrode 18, or the diameters of both heads 22, 28 can be equal. The functions of the electrodes 18, 20 will be described hereinafter.

Referring to FIG. 2, the housing 12 includes a compartment 38 having a rectangular-shaped first chamber 40, a rectangular-shaped second chamber 42 positioned intermediate the first chamber 40 and the aperture 34, and a rectangular-shaped third chamber 44 positioned intermediate the first chamber 40 and the aperture 36. The aperture 34 extends from the first end 14 of the housing 12 to the second chamber 42 and the aperture 36 extends from the second end 16 of the housing 12 to the third chamber 44. Alternatively, the second chamber 42 need not be included and, in such case, the aperture 34 may extend from the first end 14 of the housing 12 to the first chamber 40.

Referring to FIG. 1, the housing 12 includes a hexagonal-shaped access panel 46 that is sized and shaped to enclose the compartment 38. Referring to FIG. 2, the housing 12 includes a plurality of apertures 48 having internal threads (not shown in the Figures), while the panel 46 includes a plurality of apertures (not shown in the Figures), each of which correspond with one of the apertures 48 of the housing 12. Each of the apertures 48 of the housing 12 and each of a corresponding one of the apertures of the panel 46 receives one of a plurality of screws 50, which secure the panel 46 to the housing 12 (not shown in FIG. 2, but see FIG. 1). Alternatively, the panel 46 can be secured to the housing 12 by other means known in the art, such as adhesives or by the use of snap-tabs formed on the panel 46 and corresponding tab slots formed in the housing 12 (not shown in the Figures).

Referring to FIG. 2, the stimulator includes a printed circuit board 52 that is positioned within the first chamber 40 of the housing 12, and a power supply 54 that which is positioned within the third chamber 44 of the housing 12 and is connected electrically to the printed circuit board 52. A wire 56 runs through the aperture 34 and the second chamber 42 and electrically connects the first electrode 18 to the printed circuit board 52 and the power supply 54. Similarly, a wire 58 runs through the second aperture 36 and the third chamber 44 and electrically connects the second electrode 20 to the printed circuit board 52 and the power supply 54.

Still referring to FIG. 2, the printed circuit board 52 includes a first potentiometer 60 and a second potentiometer 62 that extend upwardly therefrom, a third potentiometer 64 and a fourth potentiometer 66 that extend outwardly from one side 68 of the housing 12, and a slide switch 70. The potentiometer 64 is connected electrically to the first electrode 18 and the printed circuit board 52, while the potentiometer 66 is connected electrically to the second electrode 20 and the printed circuit board 52. The functions of the potentiometers 60, 62, the potentiometers 64, 66, and the switch 70 shall be described hereinafter.

Referring to FIGS. 1 and 2, a first light emitting diode (LED) 72 and a second LED 74 are mounted on the printed circuit board 52. Each of the LEDs 72, 74 protrude through a corresponding aperture formed within the panel 46 (not shown in the Figures) when the panel 46 is fastened to the housing 12 (not shown in FIG. 2, but see FIG. 1). The stimulator 10 includes a grounding wire 76, one end of which is connected to the printed circuit board 52, and the other end of which includes a connecting pin 78. A grounding electrode 80, which includes a rectangular-shaped pad 82 and a wire 84 having a connecting pin 86, is connected to the grounding wire 76, such that the pins 78, 86 are sized and shaped to mechanically and electrically connect with one another. Preferably, the pad 82 of the grounding electrode 80 has a self-adhesive surface (not shown in the Figures). The function of the grounding electrode 80 shall be described hereinafter.

Preferably, the housing 12 and the panel 46 are each hexagonal in shape. However, the housing 12 and the panel 46 may each consist of other shapes and sizes, such as rectangular, elliptical or conical in shape. The electrodes 18, 20 are, preferably, circular in shape, but they can consist of other shapes and sizes, such as square, rectangular, elliptical or triangular in shape.

Preferably, the housing 12 is manufactured from an injection-molded polymer plastic material. Alternatively, the housing 12 can be manufactured from other materials. The electrodes 18, 20 are preferably manufactured from an electrically conductive and biocompatible material, such as stainless steel or aluminum. Alternatively, the electrodes 18, 20 can be made from other materials.

Preferably, the printed circuit board 52 is obtained commercially from Johari Digital Healthcare Ltd.'s (of Rajasthan, India; web site joharidigital.com) TENS 2500 device, model number ZZA250T. Alternatively, the printed circuit board 52 can be supplied by other manufacturers and/or be characterized by other model and part numbers.

Preferably, the power supply 54 consists of a standard 9-volt battery. Alternatively, the power supply 54 can consist of other types of batteries, such as, for example, a button style "watch" battery, which can be mounted on or off the printed circuit board 52.

The grounding electrode 80 is commercially available and may be obtained from a healthcare supplier or pharmacy. Alternatively, the grounding electrode 80 may consist of other brands and models and/or may be obtained from other manufacturers. The pad 82 of the grounding electrode 80 should be at least 2"×2" and flat, but it may consist of other shapes and sizes.

Figure 3:
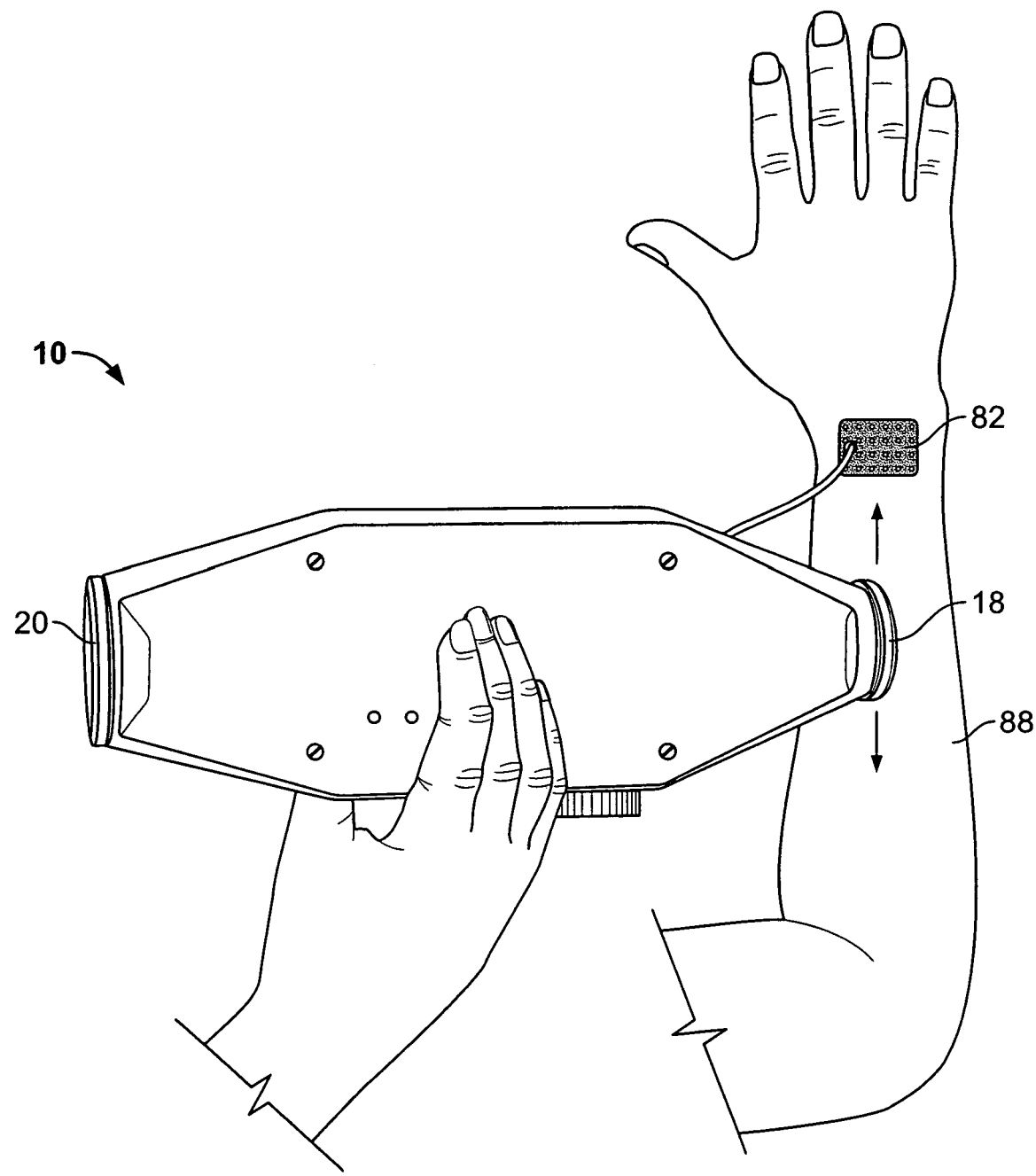
FIG. 3 is a perspective view of the stimulator shown in FIG. 1 being applied to a patient's forearm.

Referring to FIGS. 1 through 3, the stimulator 10 is implemented in conjunction with the Marcus Method disclosed in the Marcus '063 Patent, which patent has been incorporated by reference herein in its entirety. In this regard, the settings of the stimulator 10 are adjusted by a user by employing the potentiometer 60 to adjust the frequency of the applied electrical stimulus waveform, while employing the potentiometer 62 to adjust of the duty cycle of the applied stimulus waveform. The switch 70 enables a user to change the "mode" of operation of the stimulator 10 between a continuous waveform output, a burst mode which delivers a short burst of a waveform, and a modulation mode in which a continuous waveform carrier signal is amplitude modulated.

The output current of the stimulator 10 can vary from 0 mA to about 200 mA. Experiments have shown that optimal detection of pain varies from person to person, with generally larger and heavier people requiring more current to obtain the same results as a smaller and lighter person. Experiments have also shown that the waveform that produces the best response (i.e., the most accurate location of the pain source) is a continuous square wave, with a 50% duty cycle and a frequency in the range from about 100 Hz to about 150 Hz. The output waveform frequency of the stimulator 10 can be adjusted over a range of 0 Hz to about 200 Hz with variable duty cycle.

The electrical signal generated by the stimulator 10 is not limited to the shape of a square wave for the output waveform. For instance, the output waveform can be any periodic waveform, such as square waveform, a triangular waveform, a sinusoidal waveform, or a saw tooth waveform, or any combination thereof. In addition, the output waveform can be amplitude modulated. For example, the carrier frequency can be a sinusoidal waveform falling within a frequency range of about 1500 Hz to about 5000 Hz amplitude modulated with a sinusoidal waveform which produces a beat frequency in the range of about 1 Hz to about 200 Hz. Alternatively, the carrier waveform can be any periodic waveform, such as a square waveform, a triangular waveform, a sinusoidal waveform, or a saw tooth waveform, and likewise the amplitude modulating waveform can be any periodic waveform, such as a square waveform, a triangular waveform, a sinusoidal waveform, or a saw tooth waveform, or any combination thereof.

Next, the pin 86 of the grounding electrode 80 is attached to the pin 78 of the grounding wire 76. The pad 82 is adhered to the skin of a patient, such as on the patient's arm 88 (see FIG. 3). Preferably, the grounding electrode 80 is placed in the vicinity of the suspected trigger point and should be properly secured in order to maximize patient comfort. The grounding electrode 80 acts as a negative terminal for the stimulator 10.

At this stage, a user must determine which of the electrodes 18, 20 will be used for diagnosis. For example, the first electrode 18, which is, preferably, the smaller of the electrodes 18, 20, can be used to stimulate small muscles, such as the flexor digitorum superficialis muscle (which is located in the arm) or small muscle groups. The second electrode 20, which is, preferably, the larger of the electrodes 18, 20, can be used for stimulating large muscles, such as the trapezius muscle (which is located in the upper back) or larger muscle groups. In addition, the second electrode 20 can be used to establish the general location of a muscle group containing a potential myofascial pain trigger point, while the electrode 18 can be used to find a particular muscle within the muscle group that is the source of the myofascial pain trigger point.

It is noted that the heads 22, 28 of the electrodes 18, 20 are preferably sized and shaped to meet the present FDA approved contact area to field strength requirements. For example, the head 22 of the electrode 18 is, preferably, 1 inch in diameter and approximately 0.785 square inches in surface area, while the head 28 of the second electrode 20 is, preferably, 1.5 inches in diameter and approximately 1.767 square inches in surface area. These sizes are used in order to minimize the possibility of a patient experiencing a burning sensation as would be the case with an electrode having small surface area. However, it is noted that the diameter and surface area of the heads 22, 28 of the electrodes 18, 20 can each be greater or smaller than those previously listed.

If the first electrode 18 is to be used for diagnosis, then the user turns the potentiometer 64 in order to turn on and increase or decrease the power (i.e., current) of a signal to be applied to the first electrode 18. Similarly, if the second electrode 20 is to be used for diagnosis, then the user turns the potentiometer 66 in order to turn on and increase or decrease the power (i.e., current) of a signal to be applied to the second electrode 20. The power supply 54 generates an electrical current to each of the electrodes 18, 20. Each of the electrodes 18, 20 act as a positive terminal of the stimulator 10.

The LED 72 functions as an on/off indicator of the stimulator 10, while the LED 74 functions as a low battery indicator. Alternatively, the stimulator 10 need not include either or both of the LEDs 72, 74, or the stimulator may include additional LEDs used for other types of indicators (not shown in the Figures).

Once the desired settings of the stimulator 10 are set, conductive gel (not shown in the Figures) is applied to the general area of suspected pain. The electrode 18 is placed on an easily contracted muscle (i.e., a reference muscle), which for large muscles, can be, for example, the trapezius (upper back muscle). The potentiometer 64 is turned in order to increase the amperage of the electrode 18 to the minimal amount to induce a muscle contraction from the reference muscle. Once this is determined, the user can utilize the Marcus Method of locating trigger points. More particularly, the user places the contact surface 24 of the electrode 18 on the skin of the patient in the suspected location of trigger points and moves the stimulator around the suspected area of pain. If a trigger point is within such area, the electrical stimulus from the stimulator 10 will prompt a pain response from the patient, which is then recorded. The stimulator 10 is then moved to a nearby area. If the patient indicates a decrease in pain, then the location of the trigger point has been determined. It is noted that the same technique is used in connection with the second electrode 20 when diagnosing trigger points in larger muscles or muscle groups. In addition, the second electrode 20 can be used to diagnose the general location of a trigger point within a muscle group, while the second electrode 18 can be used to diagnose the specific location of the trigger point within a particular muscle of the muscle group.

Because the stimulator 10 is wireless, it is highly maneuverable and can be placed on any part of the patient's body. Furthermore, the stimulator 10 is lightweight and ergonomically designed, thereby enabling a user to use it comfortably and easily in a clinical setting. The stimulator 10 allows a physician to easily detect the responses to electrical stimuli, resulting in an accurate diagnosis of the location of pain. This provides the physician with a better understanding of the pain conditions in a patient so that medicine, massage, injections, or other appropriate remedies can be more accurately directed. Medical physicians can use the stimulator 10 for performing routine checkups or when diagnosing complaints of muscle pain in patients. Pain management specialists and physical therapists can accurately and precisely pinpoint pain and accurately and precisely direct therapies (ultrasound, electro-neural stimulation therapy, thermal therapy, massage) and therapeutic exercises. Sports medicine practitioners and physical trainers can use the stimulator 10 to diagnose and characterize injuries sustained during rigorous physical activity either in a clinical setting or outdoor/athletic environments. Pharmaceutical researchers can utilize the stimulator 10 to accurately and precisely identify pain states in the source muscle in test subjects to achieve high levels of repeatability for analgesic/pain-killer drug development.

Figure 4:
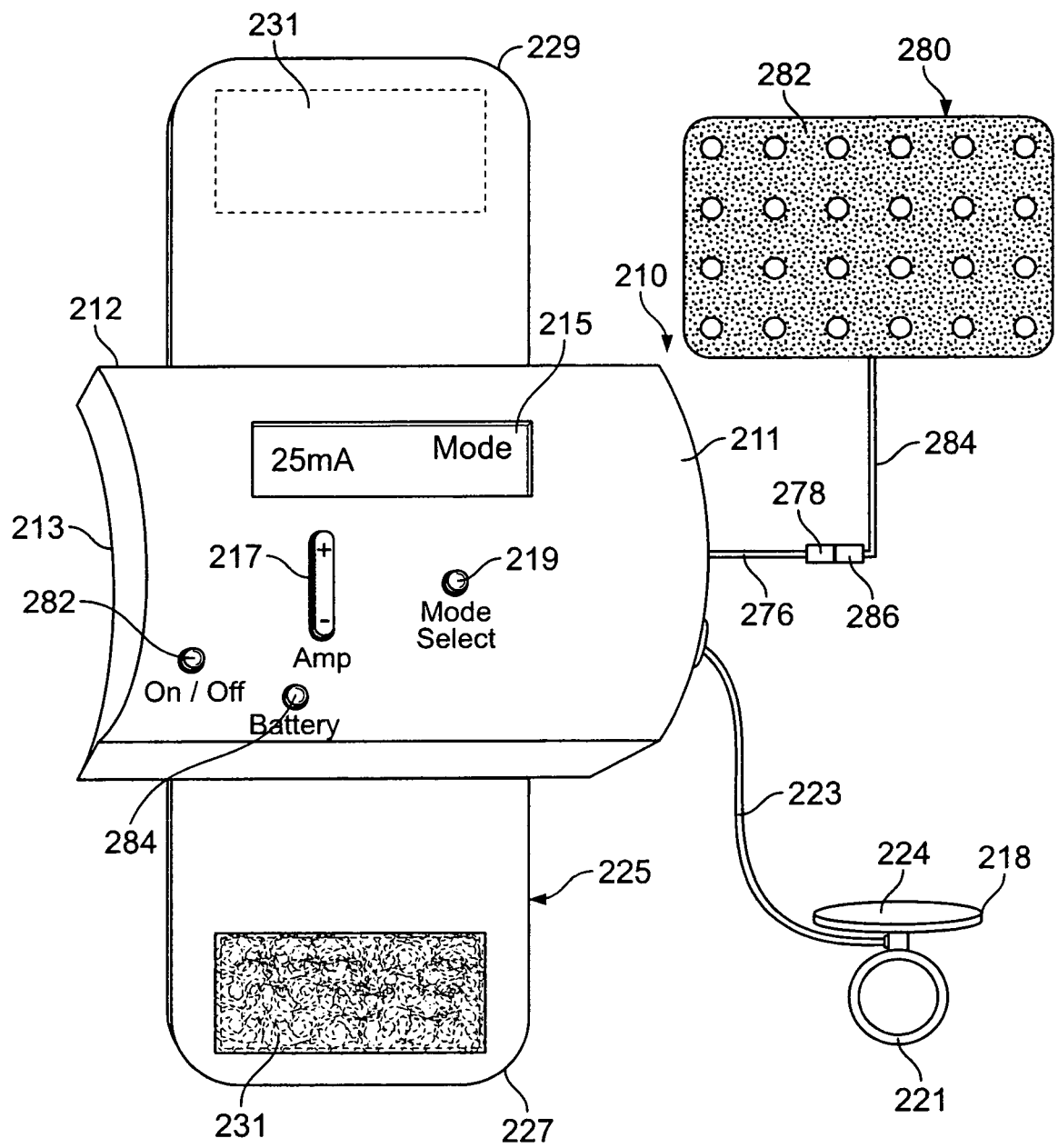
FIG. 4 is a perspective view of an electro-neural stimulator constructed in accordance with another exemplary embodiment of the present invention.

Another exemplary embodiment of the present invention is illustrated in FIG. 4. Elements illustrated in FIG. 4 that correspond to the elements described above with reference to FIGS. 1 through 3 have been designated by corresponding reference numerals increased by two hundred (200). In addition, elements illustrated in FIGS. 1 through 3 that do not correspond to the elements described herein with reference to FIGS. 1 through 3 are designated by odd reference numbers starting with reference numeral 211. The embodiment of FIG. 4 operates in the same manner as the embodiment of FIGS. 1 through 3, unless it is otherwise stated.

Referring to FIG. 4, an electro-neural stimulator 210 includes a rectangular-shaped housing 212 having a first surface 211 and a concave-shaped second surface 213 opposite the first surface 211, whose function shall be described hereinafter. The housing 212 houses a printed circuit board (not shown in the Figures), the components of which are identical or similar to the components of printed circuit board 52 of the stimulator 10 described above. The first surface 211 of the housing 12 includes various controls and indicators, such as an LCD display 215, an amperage toggle switch 217, a mode select button 219, and a pair of LED indicators 272, 274.

Still referring to FIG. 4, the stimulator includes a circular-shaped electrode 218 having a contact surface 224 mounted to a circular-shaped ring 221. The functions of the electrode 218 and the ring 221 shall be described hereinafter. A wire 223 electrically connects the electrode 218 to the printed circuit board (not shown in the Figures). One end of a grounding wire 276 is connected to the printed circuit board (not shown in the Figures), while a connecting pin 278 is connected to the other end of the grounding wire 276. A grounding electrode 280, which includes a rectangular-shaped pad 282 and a wire 284 having a pin 286, is connected to the grounding wire 276, such that the pins 278, 286 are sized and shaped to mechanically and electrically connect with one another.

Still referring to FIG. 4, a strap 225 having a first end 227 and a second end 229 opposite the first end 227 is fastened to the housing 212. The ends 227, 229 include VELCRO® brand fasteners 231 so that the ends 227, 229 may be fastened to one another. Other fastening means known in the art may be utilized to fasten the ends 227, 229 of the strap 225 to one another, such as snaps, adjustable belts and buckles, etc.

Figure 5:
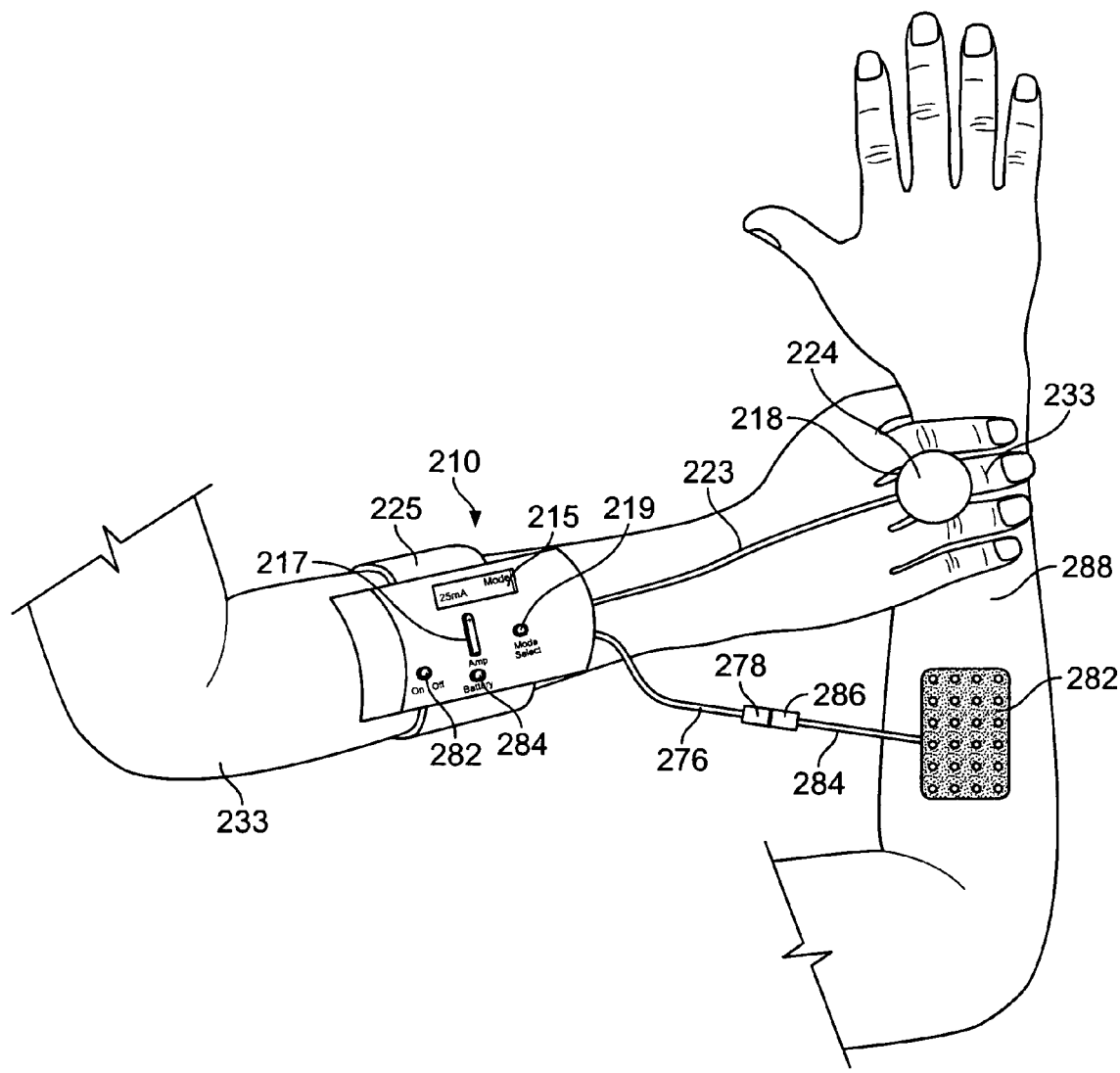
FIG. 5 is a perspective view of the stimulator shown in FIG. 4 strapped to a physician's arm and being applied to a patient's forearm.

Referring to FIGS. 4 and 5, the stimulator 210 operates in the following manner. First, the stimulator 210 is attached to the forearm 233 of a user and is secured thereto by the fastening the ends 227, 229 of the strap 225. The stimulator 210 can also be strapped any other portion of the user's body, such as around the tricep or the waist, as desired. Alternatively, the housing 212 may employ a belt clip for securing it to a user's belt (not shown in the Figures). The concave surface 213 of the housing 212 is sized and shaped so that it contours with the arm 231 of the user, thereby providing a more comfortable fit. Next, the ring 221 is slipped on a finger 233 of the user, whereby the contact surface 224 of the electrode 218 is positioned distal from the back side of the user's hand. Alternatively, the electrode 218 can be positioned on the palm side of the hand (not shown in the Figures). The wire 223 is of sufficient length such that the electrode 218 may be positioned on the user's hand in a comfortable manner.

Next, the settings of the stimulator 210 are adjusted. The output current of the stimulator 210 can vary from 0-200 mA and is manually selected by depressing the amperage toggle switch 217. The output waveform frequency of the stimulator 210 can be set by depressing the mode selected button 219. The LCD screen 215 provides a visual display of the selected amperage, mode, and other pertinent indicators. The LED 272 functions as an on/off indicator of the stimulator 210, while the LED 274 functions as a low battery indicator. Alternatively, the stimulator 210 need not include either or both of the LEDs 272, 274 and such information can be displayed on the LCD screen 215, or the stimulator may also include additional LEDs used for other types of indicators (not shown in the Figures).

Next, the pin 286 of the grounding electrode 280 is attached to the pin 278 of the grounding wire 276 of the housing 212. The pad 282 is adhered to the skin of a patient, such as on the patient's arm 302. Preferably, the grounding electrode 280 is placed in the vicinity of the suspected trigger point and should be properly secured in order to maximize patient comfort.

Once the desired settings of the stimulator 10 are set, conductive gel (not shown in the Figures) is applied to the general area of suspected pain. The contact surface 224 of the electrode 218 is placed on a reference muscle, such as the trapezium. The amperage toggle switch 217 is depressed in order to achieve the desired amperage of the electrode 218 to the minimal amount to induce a muscle contraction from the reference muscle. Once this is determined, the user can utilize the Marcus Method by placing the contact surface 224 of the electrode 218 on the skin of the patient in the suspected location of trigger points and move the stimulator around the suspected area of pain. If a trigger point is within such area, the electrical stimulus from the stimulator 210 will prompt a pain response from the patient, which is then recorded. The stimulator 210 is then moved to a nearby area. If the patient indicates a decrease in pain, then the location of the trigger point has been determined and appropriate treatment can be initiated.

The stimulator 210 is wireless, highly maneuverable and can be used to diagnose any part of the patient's body. Furthermore, the stimulator 210 is lightweight and ergonomically designed, thereby enabling a physician to use it comfortably and easily in a clinical setting. It is also noteworthy that the position of the electrode 218 on the physician's hand as shown in FIG. 5 allows the physician to freely alternate between manual palpation of the patient's muscles with his fingertips and the application of the electrode 218 for applying electrical stimulus to the patient's muscles. Accordingly, the stimulator 210 gives the physician maximum flexibility in diagnosing trigger points.

Figure 6:
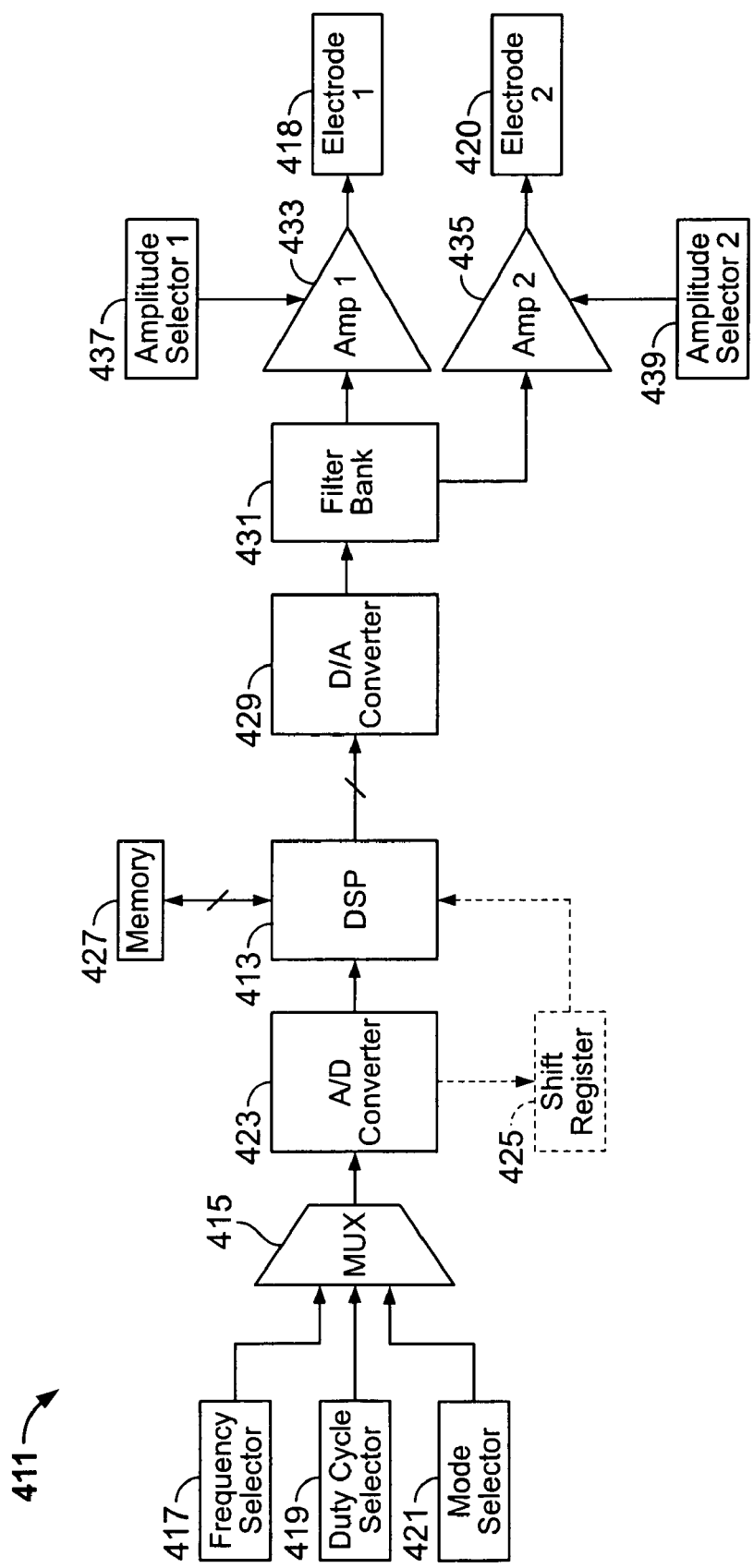
FIG. 6 is an electrical block diagram of a digital signal processor (DSP) employed by the stimulators shown in FIGS. 1-5 in accordance with another exemplary embodiment of the present invention.

Referring to FIG. 6, an alternate embodiment of the circuitry employed in the electro-neural stimulators 10, 210 shown in FIGS. 1 through 5. Elements illustrated in FIG. 6 that correspond to the elements described above with reference to FIGS. 1 through 3 have been designated by corresponding reference numerals increased by four hundred (400). In addition, elements illustrated in FIG. 6 that do not correspond to the elements described herein with reference to FIGS. 1 through 5 are designated by odd reference numbers starting with reference numeral 411. The embodiment of FIG. 6 operates in the same manner as the embodiment of FIGS. 1 through 5, unless it is otherwise stated.

FIG. 6 is an electrical block diagram of alternate electrical components of the stimulators 10, 210 constructed in accordance with another exemplary embodiment of the present invention. Instead of employing an analog circuit to implement a waveform generator, the stimulator includes a circuit 411 which employs a digital signal processor (DSP) 413 to simulate a digital version of the waveform generator. The circuitry surrounding the DSP 413 includes an analog multiplexer 415, a frequency selector 417, a duty cycle selector 419 and a mode selector 421, each of which is electrically connected to the multiplexer 415, an analog-to-digital converter (A/D) 423 electrically connected to the multiplexer 415, an optional shift register 425 electrically connected to the A/D 423 and to the DSP 413, a memory module 427 electrically connected to the DSP 413, a digital-to-analog converter (D/A) 429 electrically connected to the DSP 413, a filter bank 431 electrically connected to the D/A 429, a pair of power amplifiers 433, 435 each of which is electrically connected to the filter bank 431, a first amplitude selector 437 electrically connected to the power amplifier 433, and a second amplitude selector 439 electrically connected to the power amplifier 435. The power amplifier 433 is electrically connected to a first electrode 418, while the power amplifier 435 is electrically connected to a second electrode 420.

The output voltages of each of the frequency selector 417, the duty cycle selector 419, and the mode selector 421 are sampled in a time-division multiplexed fashion by the multiplexer 415. The output of the multiplexer 415 is sampled by the analog-to-digital converter (A/D) 423. The shift register 425 converts the parallel outputs of the A/D converter 423 to a serial bit stream, which is input to the DSP 413. The DSP 413 interfaces with the memory 427, which may be a combination of random access memory for storing intermediate calculations and executing a waveform generation program, and a non-volatile FLASH portion of the memory 427, which may store waveforms and/or a program for forming the waveforms. The output of the DSP 413, applies a discrete version of the waveforms to be applied, which is converted to analog form by the D/A converter 429. The output of the D/A converter 429 is fed to the filter bank 431, which can filter out quantization noise and other distortions. The output of the filter bank 431 is fed to the power amplifiers 433, 435, which outputs a signal capable of applying RMS currents in the range of 0-200 mA to the electrodes 418, 420 by adjusting the amplitude selectors 437, 439.

It will be understood that the embodiments described herein are merely exemplary and that a person skilled in the art may make many variations and modifications without departing from the spirit and scope of the invention. All such variations and modifications are intended to be included within the scope of the present invention as defined in the appended claims.

What is claimed is:

1. A self-contained apparatus for identifying a source of a patient's muscular pain, comprising:

a portable housing having compactly arranged opposite first and second ends and a grippable portion between said ends, said portable housing being sized and shaped so that it may be conveniently carried in the hand of a human being;

generating means, contained within said housing, said generating means including a digital signal processor for generating an electrical carrier wave signal having a carrier wave frequency in the range of about 1500 Hz to about 5000 Hz and a periodic waveform selected from the group of waveforms consisting of a square waveform, a triangular waveform, a sinusoidal waveform, and a sawtooth waveform, an electrical modulating signal having a modulating signal frequency, and an electrical output signal having a current amplitude sufficient to stimulate contraction of a patient's muscle, the electrical output signal including a combination of the electrical carrier wave signal and the electrical modulating signal, the periodic waveform of the electrical carrier output signal being the periodic waveform of the electrical carrier wave signal and the electrical carrier wave signal being amplitude-modulated by the electrical modulating signal so as to produce an output signal frequency in the electrical output signal, the output signal frequency being the difference between the carrier wave frequency and the modulating signal frequency;

frequency selection means for selecting an output signal frequency for an electrical output signal generated by said generating means, the output signal frequency being in the range of greater than 0 Hz to about 200 Hz;

amplitude selection means for selecting a current amplitude for an electrical signal generated by said generating means, the current amplitude being within the range of greater than 0 mA to about 200 mA;

first and second metal electrodes affixed, respectively, to said first and second ends of said housing said first and second metal electrodes having respective substantially flat first and second contact surfaces electrically connected to said generating means so as to conduct an electrical output signal generated thereby, said first contact surface being smaller in area than said second contact surface;

a grounding electrode attachable to the patient for providing a grounding path for an electrical output signal generated by said generating means; and a power source for providing power to said generating means, said power source being a 9-volt battery contained within said housing, said generating means being arranged to generate a current amplitude for an electrical signal generated by said generating means within the range of greater than 0 mA to about 200 mA when said power source provides a voltage of 9 volts to said generating means.

2. The apparatus of claim 1, further comprising means for (i) identifying a suspected area of muscular pain on a patient's body, (ii) positioning said electrode in contact with the patient's body in the suspected area of pain, (iii) recording the patient's reported level of discomfort and/or pain response when an electrical signal is conducted by said electrode, and (iv) repeatedly re-positioning said electrode in contact with the patient's body in response to the patient's reported level of discomfort and/or pain response so as to identify a location of maximum reported discomfort and/or maximum pain response.

* * * * *